US 6,554,472 B1

(12) United States Patent
Dietz et al.

(10) Patent No.: US 6,554,472 B1
(45) Date of Patent: Apr. 29, 2003

(54) X-RAY POSITIONER WITH LEAD SHIELD PROTECTION DEVICE

(75) Inventors: Douglas P. Dietz, Pewaukee, WI (US); Michael J. Barber, Mequon, WI (US)

(73) Assignee: GE Medical Systems Global Technology, Waukesha, WI (US)

( * ) Notice: Subject to any disclaimer, the term of this patent is extended or adjusted under 35 U.S.C. 154(b) by 0 days.

(21) Appl. No.: 10/063,645

(22) Filed: May 7, 2002

Related U.S. Application Data (60) Provisional application No. 60/334,745, filed on Nov. 15, 2001.

(51) Int. Cl.[7] ................................................. H05G 1/02
(52) U.S. Cl. ........................ 378/197; 378/189; 378/203
(58) Field of Search ................................ 378/189, 193, 378/196, 197, 198, 203; 250/515.1

(56) References Cited

U.S. PATENT DOCUMENTS

| | | | | |
|---|---|---|---|---|
| 4,062,518 A | * | 12/1977 | Stivender et al. ........... 378/208 |
| 4,581,538 A | * | 4/1986 | Lenhart ..................... 250/515.1 |
| 4,807,273 A | * | 2/1989 | Haendle ....................... 378/197 |
| 4,894,855 A | | 1/1990 | Kresse ........................ 378/196 |
| 5,835,558 A | * | 11/1998 | Maschke ..................... 378/198 |
| 6,200,024 B1 | | 3/2001 | Negrelli ...................... 378/197 |
| 6,325,538 B1 | * | 12/2001 | Heesch ........................ 378/203 |
| 6,435,715 B1 | * | 8/2002 | Betz et al. ................... 378/197 |

* cited by examiner

*Primary Examiner*—Drew A. Dunn
(74) *Attorney, Agent, or Firm*—Quarles & Brady LLP; Carl Horton (57) ABSTRACT

An x-ray imaging system is presenting having two independently articulated arms supporting an x-ray tube and x-ray detector, respectively. The detector is included in a detector assembly that further includes a display and user interface for controlling the arms. The detector assembly further includes at least one lead shield that is extendable to protect an operator stationed at the display during use.

20 Claims, 8 Drawing Sheets

X-RAY POSITIONER WITH LEAD SHIELD PROTECTION DEVICE

CROSS REFERENCE TO RELATED APPLICATIONS

The present application claims priority to U.S. Provisional Patent Application Ser. No. 60/334,745 and entitled "X-RAY POSITIONER WITH SIDE-MOUNTED, INDEPENDENTLY ARTICULATED ARMS" filed on Nov. 15, 2001, the disclosure of which is hereby incorporated by reference as if set forth in its entirety herein.

BACKGROUND OF INVENTION

This application relates to medical x-ray positioners and in particular to a positioner using independently articulated arms to support the x-ray source and x-ray detector.

Conventional x-ray positioners provide mechanical supports to hold an x-ray source and x-ray detector in opposition about a patient for a limited number of specific procedures. For procedures in which the patient is standing, the x-ray source may be attached to a pillar allowing adjustment in its height as directed toward an x-ray detector attached to an opposing wall or a second similar pillar. For procedures in which the patient is supine, the x-ray source and detector may, be attached to opposite sides of a patient table. Alternatively the x-ray source and the detector may be attached to opposite ends of a C-arm which is supported by a sliding collar allowing the angle of the x-rays through the patient to be varied.

Multi-axis robotic arms, positioned above and below the patient table, have been proposed to provide support for the x-ray source and x-ray detector such as may reduce interference between the support structure and other equipment and personnel. See, for example, U.S. Pat. No. 6,200,024 to Negrelli citing U.S. Pat. No. 4,894,855 to Kresse.

Such systems require complex multi-axis movement for simple adjustments of the x-ray tube and detector in angulation or translation, and appear to have limited utility for certain common x-ray procedures such as those requiring the patient to stand. Further such systems make it difficult or impossible to swap the location of the x-ray source from beneath the patient to above the patient, when the patient is supine, and an improved image might thereby be obtained.

Currently, an operator stationed at conventional systems in the path of x-ray scatter is required to wear a lead vest that protects the operator during use. Because such vests are bulky and heavy, an operator is likely to experience fatigue over time.

SUMMARY OF INVENTION

The present invention provides an x-ray imaging system having an integrated shield assembly to protect both the operator and system components from x-ray scatter. Generally the invention provides an x-ray imaging system having an x-ray source producing an x-ray beam directed along a source axis, and an x-ray detector assembly including a frame supporting a detector for detecting x-rays received along a detector axis aligned with the source axis, and a user interface mounted to the frame. A first and second articulated arm are provided, each having at least two independent axes of motion. The first articulated arm holds the x-ray source at its first end, and the second articulated arm holds the x-ray detector at its first end. At least one x-ray blocking shield is mounted to the detector assembly so as to be articulated between a retracted and extended configuration.

DETAILED DESCRIPTION

Figure 1:
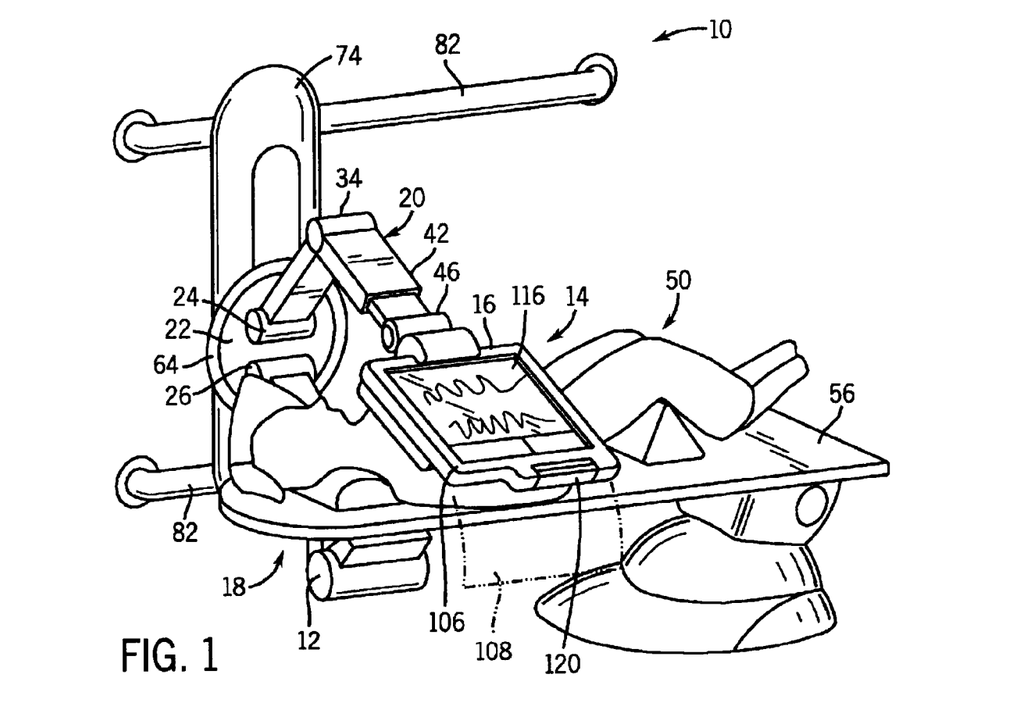
FIG. 1 is a perspective view of one embodiment of the positioner of the present invention showing offset mounting of two independently articulated arms holding an x-ray source and x-ray detector assembly, respectively.

Referring now to FIG. 1, a multi-mode x-ray positioner 10 per the present invention provides an x-ray source 12 and an x-ray detector 14. The x-ray source 12 generally includes an x-ray tube, the necessary cooling components, collimators, and shielding as will be understood to those of ordinary skill in the art. The x-ray detector 14 may be a lightweight flat panel detector such as may be fabricated as an array of detectors, an amorphous silicon detector panel or other imaging device. The x-ray detector is part of a detector assembly 16 to be described in greater detail below.

The x-ray source 12 directs an x-ray beam generally along a central ray 13 whereas the x-ray detector 14 receives x-rays generally along a central ray 15 normal to the surface thereof. A patient 50 may be supported supine on a table 56 so as to be aligned with the central rays 13 and 15. For this purpose, the table 56 is composed of a radiotranslucent material of a type well known in the art.

Figure 4:
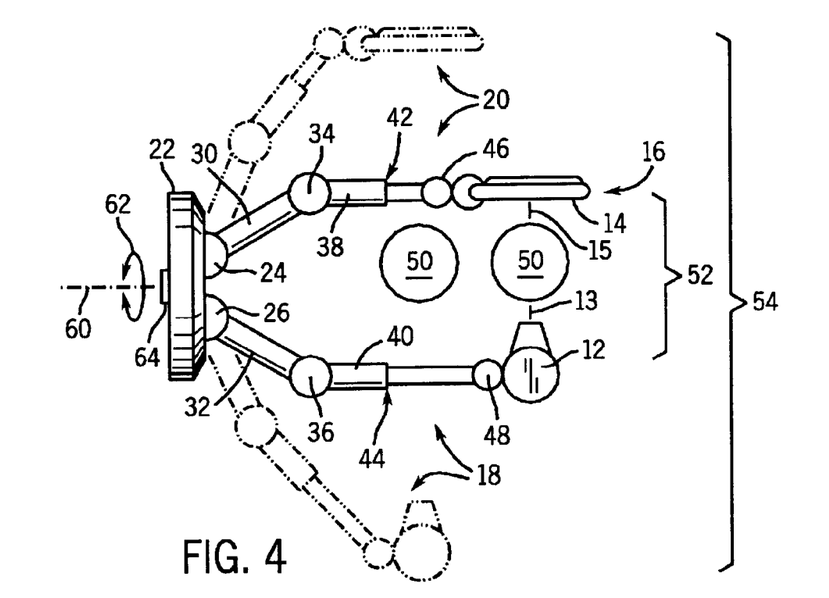
FIG. 4 is a view (top or side) of the articulated arms of the FIG. 1 showing, in phantom, arm movement implementing an increased source-to-detector distance.

Referring also to FIG. 4, each of the x-ray source 12 and the x-ray detector 14 are held, respectively, on separate articulated robot arms 18 and 20. The arms 18 and 20 are attached at a first end to a base 22, the latter preferably supported against a vertical surface with the arms extending laterally therefrom.

The arms 18 and 20 attach to the base 22 at shoulder axes 26 and 24, respectively. Each shoulder axes 26 and 24 provides angulation of its respective arm 18 or 20 about parallel axes extending generally along the plane of the base 22, the latter being parallel to a vertical plane defining the surface to which the base 22 is attached. Generally the term "axis" henceforth will refer both to a mechanical joint and the mathematical vector describing movement of that joint. The particular meaning will be evident from context.

Attached to and extending from shoulder axes 24 and 26 are upper arms 30 and 32, respectively, which terminate in elbow axes 34 and 36, respectively, each also providing for angulation along parallel axes also parallel to axes 24 and 26. Forearms 38 and 40 extend from elbow axes 34 and 36, respectively, and the latter which provide telescoping extension axes 42 and 44 permitting translation movement of wrist axes 46 and 48 along the length of the forearms 38 and 40.

Wrist axes 46 and 48 provide angulation about parallel axes also parallel to axes 24 and 26 and connect, respectively, to the x-ray detector assembly 16 and x-ray source 12. It is to be understood that the x-ray source and x-ray detector assembly are not limited to mounting on a particular arm and may be replaced by other devices to meet other clinical needs.

It will be understood from this description that each of the arms has four axes of motion comprised of shoulder axes 24, elbow axis 34 and wrist axis 46 and extension axis 42, for arm 20 and shoulder axes 26, elbow axis 36, and wrist axis 48, and extension axis 44 for arm 18. Generally, motion of shoulder axes 24 and 26 control the angle of upper arms 30 and 32 and the position of elbow axes 34 and 36 with respect to shoulder axes 24 and 26. Likewise, motion of elbow axes 34 and 36 control the angle of forearms 38 and 40 and the position of wrist axes 46 and 48 with respect to the elbow axes 34 and 36. Motion of extension axes 42 and 44 control the separation of elbow axis 34 and wrist axis 46 and elbow axis 36 and wrist axis 48, respectively, and motion of wrist axes 46 and 48 control the angle of detector 14 and x-ray source 12.

Each of axes 24, 26, 34, 36, 42, 44, 46, and 48 are enabled for servo control meaning that they may be moved electronically in response to a position and/or motion signal received from the axis so that precise positioning and/or velocity control of each axis may be had through a central controller or group of interconnected controllers as will be described below.

Referring again to FIGS. 1 and 4, the arms 18 and 20 may be maneuvered to position the x-ray source 12 and detector assembly 16 in alignment on opposite sides of a patient 50 at a first source-to-detector distance 52. Subsequently, the arms 20 may be maneuvered, through a combined motion of their axes, to provide a source-to-detector distance 54 substantially greater than source-to-detector distance 52, while maintaining alignment. Such separation is accomplished principally by a combined angulation and extension of the axes 24, 26, 34, 36, 42, 44, 46, and 48 and notably does not require an axis of translation aligned with the central rays 13 and 15 of the source and detector as is typical of conventional x-ray positioners.

Referring again to FIGS. 1 and 4, the base 22 may be mounted on a waist axis 64 providing rotation about a line that is horizontal and perpendicular 60 to the plane of the base 22, the rotation as indicated by arrow 62. Thus, the arms 18 and 20 in their various source-to-detector separations 52 and 54 shown in FIG. 4 may be opposed about a substantially vertical axis (as depicted in FIG. 1) or about a horizontal axis. The horizontal axis is useful for procedures such as chest x-rays or other situations where the patient is best imaged while standing or seated. In these cases, the table 56 would be moved to a vertical configuration or moved out of the way altogether. The rotation of the base 22 about the waist axis 64, as with the other axes, is under servo control and provides single axis cranial-caudal angular adjustment.

Figure 5:
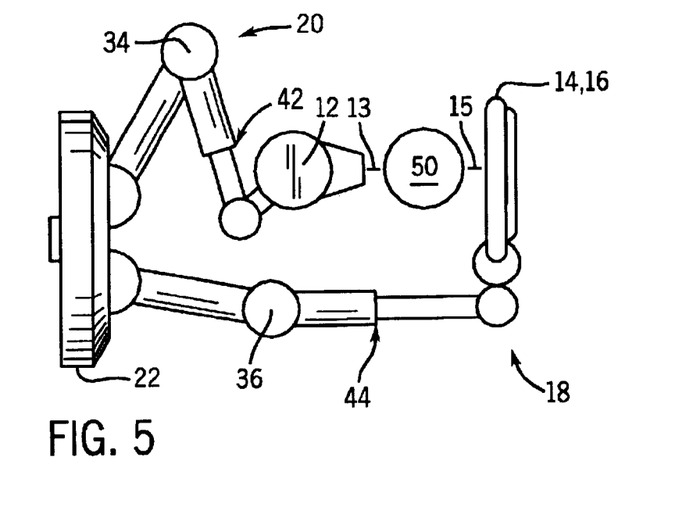
FIG. 5 is a side elevational viewing of the articulated arms of FIG. 1 showing positioning of the arms for lateral imaging.

Alternatively as shown in FIG. 5, the arms 18 and 20 may be manipulated to provide central rays 13 and 15 perpendicular to the plane of the base 22. In this case, the arms 18 and 20 are not deployed symmetrically but elbow axis 34 is moved to an acute position whereas elbow axis 36 is moved to an obtuse position with extension axis 44 fully extended and extension axis 42 fully retracted. This degree of flexibility is accomplished because each of the axes 24, 26, 34, 36, 44, 42, 46 and 48 are independently controllable.

Figure 6:
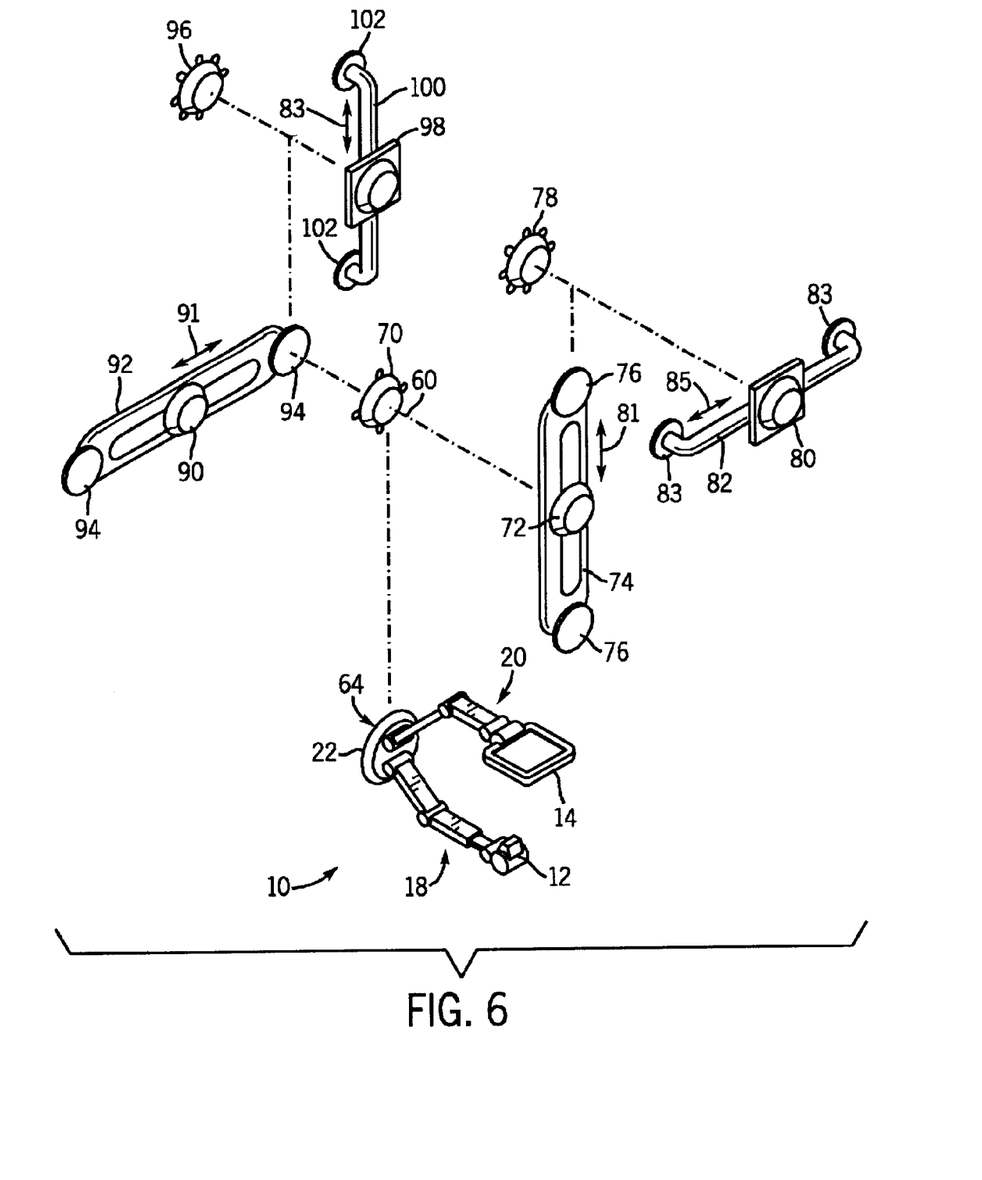
FIG. 6 is an exploded perspective diagram showing various options for adding common axes to the articulated arms of FIG. 1 for different procedures.

Referring to FIG. 6, the base 22 may be mounted directly on a wall or the like by means of stationary collar 70 receiving the waist axis 64. Alternatively, and as also shown in FIG. 6, the base 22 may be attached to a vertically translating collar 72 also receiving the waist axis 64 but providing for vertical translation along tracks 74 also under servo control to form translation axis 81. Opposed ends 76 of the track 74 may be held against the wall or vertical surface by stationary collars 78 (only one of which is shown for clarity) similar to stationary collar 70. The translation axis 81 allows single axis elevation of the x-ray source 12 and x-ray detector 16.

Alternatively, the end 76 may be received by horizontally translating collars 80 moving horizontally along tracks 82 so as to provide a horizontal servo control translation axis 85 for the tracks 74, the base 22, and thus the arms 18 and 20.

In an alternative configuration, the base 22 may be mounted to horizontally translating collar 90 of the tracks 92 positioned to extend horizontally along axis 91. The ends 94 of the tracks 92 may be attached either to a stationary collar 96, similar to stationary collars 78 or to horizontally vertically collars 98 but with the track 100 positioned to move along vertical axis 83, the latter having its ends 102 fixed to a stationary surface such as a wall or the like. The translation axis 91 allows single axis horizontal repositioning of the x-ray source 12 and x-ray detector 16.

While the two configurations represented in tree fashion by the branches ending with the axis 85 and 83 of FIG. 6 result in the same degrees of freedom, they provide alternate evolution paths allowing the positioner 10 to be upgraded from a base system having only base 22 and arms 18 and 20 to a full featured system through the addition, respectively, of various components of vertically translating collar 72, or horizontally translating collars 90. A wiring harness system (not shown) allows each of these axes to be added to an axis controller to provide improved functionality as will be described below.

Figure 2:
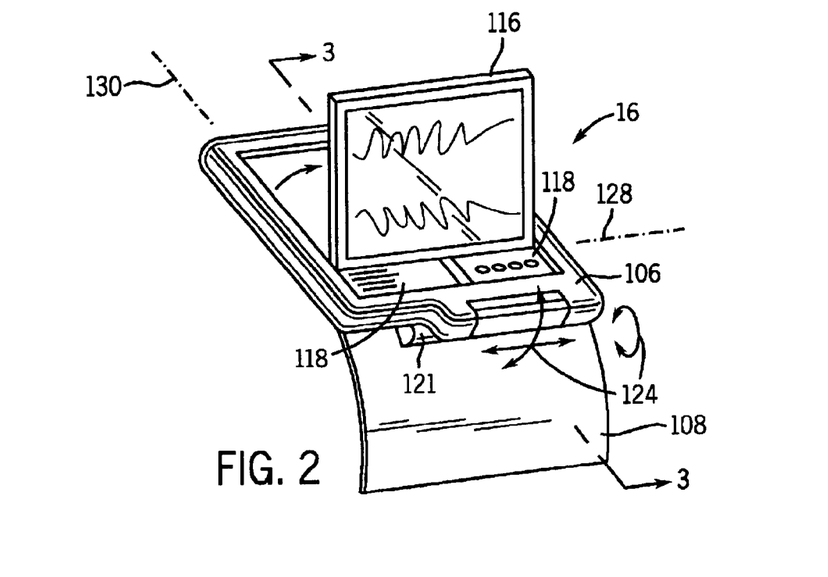
FIG. 2 is a perspective view of the detector of FIG. 1 showing a tilting upward of an integral display of the detector assembly and axes of movement of a control handle supported by the detector assembly.
Figure 3:
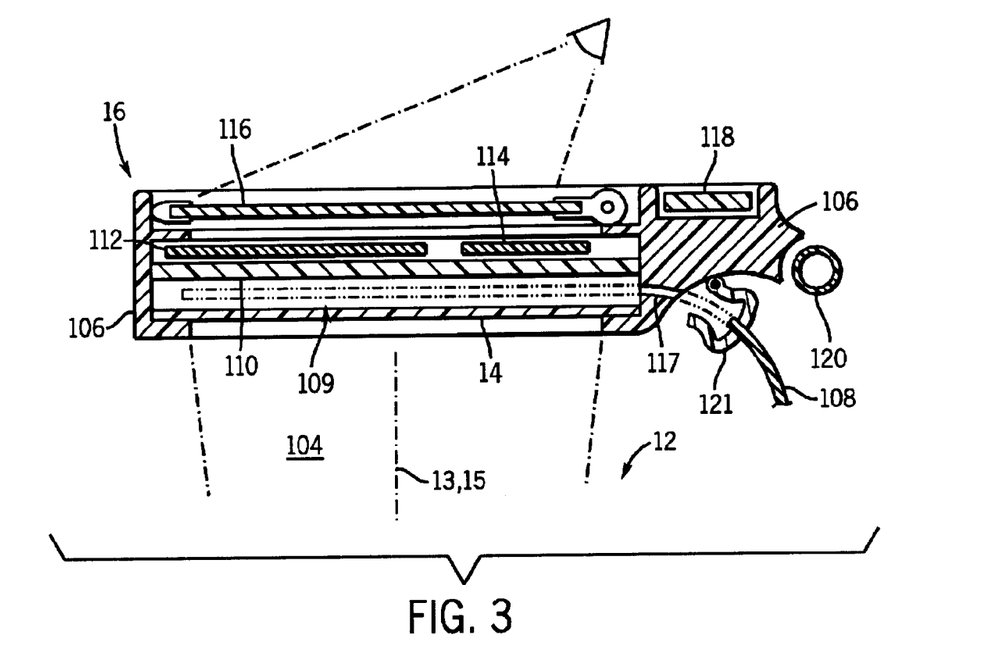
FIG. 3 is a cross-sectional view of the detector assembly of FIG. 2 taken along lines 3—3 of FIG. 2 showing the normal registration of an x-ray detector and the display incorporating a shield assembly.

Referring now to FIGS. 1, 2 and 3, the detector assembly 16 includes a flat panel x-ray detector 14 on a first surface normally facing the x-ray source 12 and held within a supporting frame 106. The flat panel x-ray detector 14 is sized to receive a collimated beam of x-rays 104 from the x-ray source 12 and positioned immediately behind the flat panel x-ray detector 14 is a blocking lead shield 110. This may-be followed by processing circuit cards 112 and 114. Following the circuit cards 112 and 114 is a flat panel display 116.

The flat panel display 116 may receive an image registered with the image received by the x-ray detector 14 for display to a human operator viewing the image from the top side of the detector assembly 16. In this configuration, the image displayed by the flat panel display 116 remains in perfect registration with the x-ray detector 14 thus eliminating confusion that can result in normal fluoroscopy systems where the image may rotate on a stationary monitor with respect to the patient as the positioner is moved. As shown in FIG. 2, in order to provide for oblique viewing angles, the flat panel display 116 may hinge upward about one of two perpendicular hinge axes 128 or 130 so as to provide better viewing for the user while still maintaining rotational registration with the patient's anatomy.

Also supported on the top side of the frame 106 is a touch screen panel 18 providing for basic level control of the x-ray system including x-ray tube voltage, exposure time, and other techniques. The front portion of the frame 106 also supports a multi-axis control handle 120 providing a number of signals depending on movement of the handle by the operator either vertically, horizontally or in rotation as shown by arrows 124 and shown also in FIG. 2. The circuit cards 112 collects data from the x-ray detector 14 for a control system to be described. The circuit card 114 provides an interface for the control system with the touch screen panel 118 and a multi-axis control handle 120.

A second blocking lead shield 108 may be attached to a portion of the supporting frame 106 and is extendable from a retracted position toward the operator during normal use as shown in FIG. 3. Shield 108 is illustrated in the extended position, with dotted lines to illustrate the retracted position. Shields 108 and 110 combine to produce a shield assembly 109 that protects both the display 116 and user interface 114 while protecting the operator who in one common operating mode will be standing at or near the detector to possibly control movement of arms 18 and 20, or view the displayed image in real-time. It should be appreciated that assembly 109 could assume several possible configurations.

In accordance with one preferred embodiment illustrated in FIG. 3, shield 110 is permanently installed in the detector assembly 16 in the path of x-ray beam travel from the detector to the interface to constantly provide protection to the user interface and to an operator who is stationed at the interface. Extendable shield 108 is mounted on a pair of guide rails (not shown) that extend longitudinally along the laterally outer edges of detector assembly 16. Frame 106 defines a channel 117 that extends between the interior of the assembly to the ambient environment to provide a pathway for the extension of shield 108.

Typically the operator will be stationed directly behind shield 108 and thus sheltered from x-ray scatter. However, in some instances it may become necessary for the operator to move to one side or the other of shield 108. The shield may thus either extend directly out the detector assembly 16 as illustrated in FIG. 1, or may alternatively be retained by a bracket 121 that is pivotally mounted onto the detector assembly 16. In particular, the distal end of shield 108 may have an increased thickness to capture the shield within bracket 121 when in the fully extended position. Thus shield 108 is thus able to hinge when in its fully extended position as illustrated in FIGS. 2 and 3 so as to protect the operator when the operator is stationed slightly off-center from shield 108. Furthermore, it should be appreciated that bracket 121 may be attached to frame 16 so as to translate laterally with respect to the detector assembly 16.

It should be appreciated that the term "longitudinal" refers to the direction of extension of shield 108 within the detector assembly 16 and that the term "lateral" is defined relative to the longitudinal direction. Shield 108 may thus be extended only as necessary to protect the operator who is in close proximity to the positioner 10 during use. In this regard, guide rails may include any known mechanism to enable the user to limit the amount of extension despite the gravitational forces that would otherwise act to fully extend the shield 108.

Positioner 10 thus provides the necessary isolation of x-ray scatter depending on the type of x-ray procedure being performed. For example, during x-ray RAD procedures, whereby the source 12 is positioned above the table 56 and supine patient 50 and the detector 14 is below the table, there is no need for the operator to be present and in the path of x-ray scatter as there would be no access to the interface 114 or display 116. Accordingly, the user will be stationed at a location remote from the scatter during such a procedure, and shield 108 may be retracted while shield 110 provides the necessary protection for the interface 114 and display 116.

During R&F procedures, whereby the source 12 is positioned underneath the table and the detector 14 is above the table, the present invention permits the operator to be stationed at the detector to receive real-time feedback from display 116 and provide real-time control to the positioner 10. During such a configuration, the user will extend shield 108 downwardly and slightly outwardly from the detector assembly 16. Accordingly, the shield assembly 109 enables an operator to be protected from x-ray scatter while stationed at the detector assembly 16 during an x-ray procedure without wearing a conventional lead vest.

Figure 12:
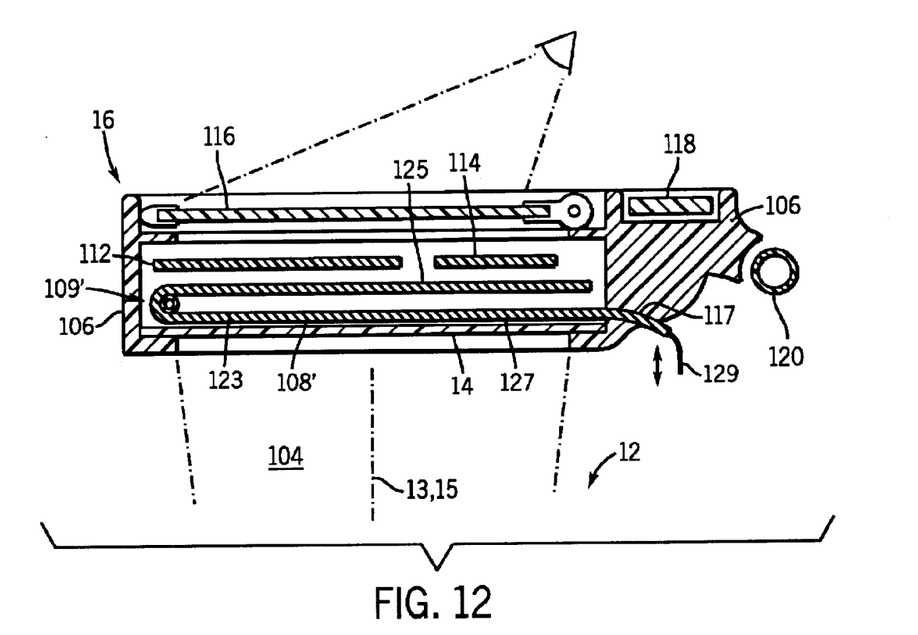
FIG. 12 is a cross sectional view of the detector assembly similar to FIG. 3 but illustrating the shield assembly in a retracted configuration in accordance with an alternate embodiment.

Referring now to FIG. 12, a shield assembly 109" includes an extendable shield 108" constructed in accordance with an alternate embodiment of the invention. In particular, shield 108" is disposed within guide rails 123 and assumes a U-shaped configuration when retracted so as to overlap itself in the direction of x-ray beam travel. Shield 108" thus includes a first longitudinally extending section 125 and a second longitudinally extending section 127. Section 127 is disposed upstream of section 125 with respect to x-ray beam travel, though it should be appreciated that this configuration may be reversed if so desired. When in the retracted position, both sections isolate the display 116 and user interface 114 from potentially damaging x-ray beams. This configuration is particularly desirable during RAD procedures, during which a significant amount of x-ray scatter will occur underneath the table, which may include a lead shield skirt surrounding the periphery of the table and extending to the floor to define an enclosure that receives a high percentage of all x-ray beams emanated from source 12. The retracted shield 109" thus provides added protection to the detector 14 and interface 114 when used in the RAD configuration.

Figure 13:
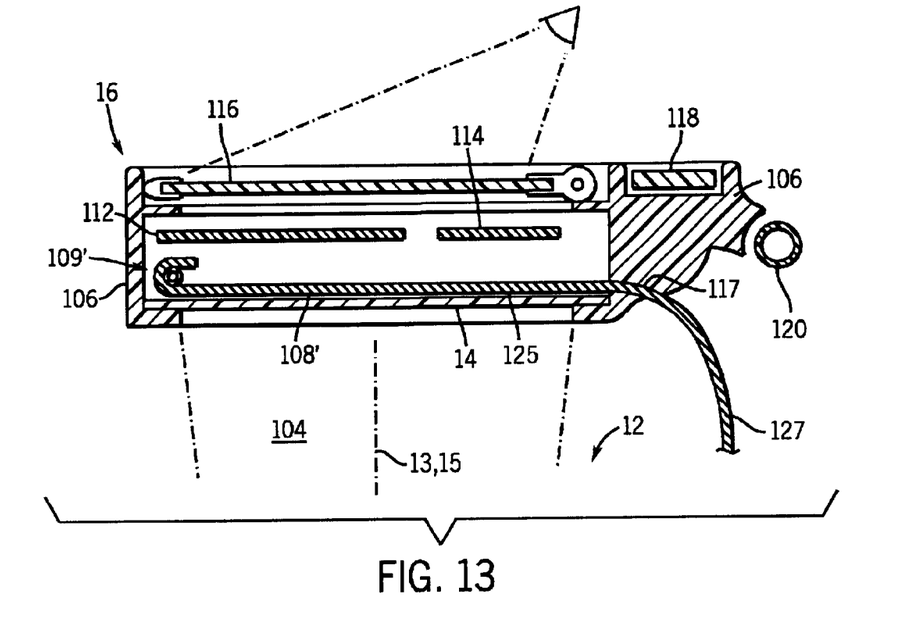
FIG. 13 is a cross sectional view of the detector assembly of FIG. 12 but with the shield assembly in an extended configuration.

A handle or pull cord 129 extends from the distal end of section 127 that extends beyond the detector assembly 116 and may be actuated by a user to extend and retract the shield 108" during use along the direction of arrow A. When the shield 108″ is extended, section 125 continues to protect the detector 14 and user interface 114, while section 127 extends downwardly and outwardly from detector assembly 116 to protect the operator who is positioned behind the detector assembly.

Figure 14:
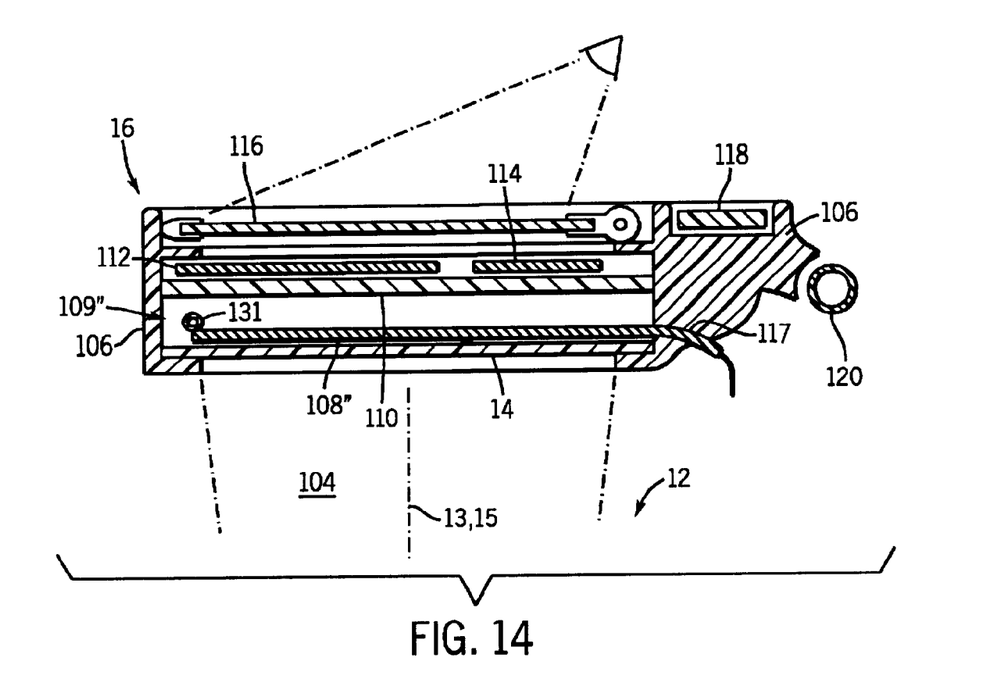
FIG. 14 is a cross sectional view of the detector assembly illustrating a shield assembly in accordance with yet another embodiment.

Referring now to FIG. 14, a shield assembly 109″″ in accordance with another embodiment of the invention includes a stationary shield 110 as described above with reference to FIG. 3. However, while shield 108 was described as being guided by rails to extend and retract, shield 108″″ as illustrated in FIG. 14 is supported by a roller 131 that mounted onto frame 106 at the opposite side of detector from channel 117. In particular, when retracted, part of the shield 108″″ is wrapped around the roller 131 while part of the shield 108″″ extends longitudinally across the detector assembly 116 such that its distal end extends beyond channel 117. Accordingly, when retracted, shield assembly 109″″ provides extra protection to the detector assembly via shields 108″″ and 110, as described above with reference to assembly 109″. However, assembly 109″″ also provides extra protection when the shield 108″″ is extended as the previously wound portion of shield 108″″ extends across the detector assembly 116. It should be appreciated that roller 131 may be configured so as to enable the operator to only partially extend shield 108″″ if desired.

It should be further appreciated that roller 131 could alternatively be disposed proximal channel 117 if so desired such that shield 110 would be dedicated to isolating detector display 116 and interface 114, while shield 108″″ would be dedicated to selectively protecting the operator when desired.

Furthermore, it should be appreciated that in some instances, an assistant to the operator may be stationed at the opposite side of table 56 from shield 108. Accordingly, positioner 10 may include an additional shield (not shown) that is extendable from the side of detector assembly 16 that is opposite channel 117. It should be appreciated that this additional shield may be mounted in any of the configurations described above with reference to shields 108, 108″, and 108″″. In this regard, the additional shield may be mounted to a base that hinges and translates laterally with respect to detector assembly 16.

Figure 7:
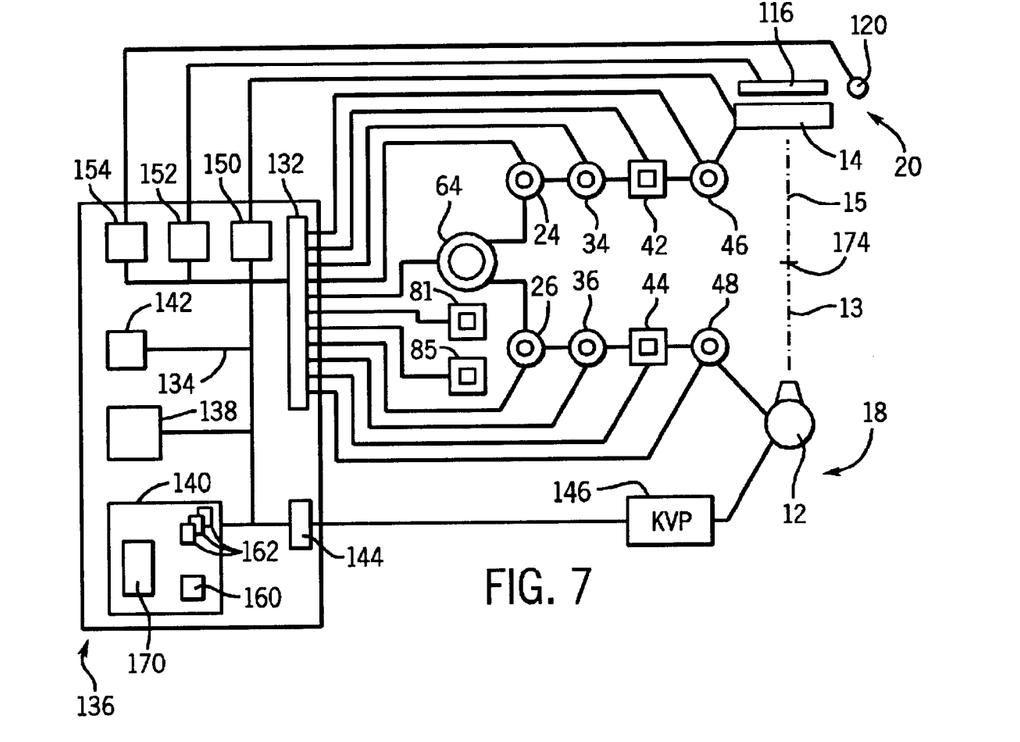
FIG. 7 is a schematic block diagram of the servo motors associated with the axis of FIGS. 1 and 6 and a controller for controlling the axes as well as the x-ray detector and x-ray source according to the present invention.

Referring now to FIG. 7, each of the different axes 24, 26, 34, 36, 42, 44, 46, 48, 64, 81, and 84 provides feedback signals and receives a command signals from an axis control interface 132 so as to provide for servo control of each axis according to techniques well known in the art. The axis control interface 132 connects to a central bus 134 of a controller 136. The controller 136 is constructed according to conventional computer architecture and includes a processor 138 communicating with the bus 134 and with memory 140 which may include both random access and magnetic disk memory or other mass storage devices. A modem 142 and/or device such as a network interface card also communicating with the bus provide pathways for downloading of information and programs into the memory 140 as will be described. The controller 136 may be a single computer or a number of interconnected computers providing the various functions and services.

The controller 136 also provides a signal through port interface 144 (also attached to bus 134) to a high voltage power supply 146 feeding the x-ray source 12 so as to provide control over current and x-ray tube voltage and on and off duty cycle. Diagnostic signals may also be received from the power supply 146 via this port interface. Additional ports interfaces 150, 152, and 154 provide communication between the central bus 134 and the control handle 120, the x-ray detector 14, the flat panel display 116, and the touch screen panel 118 described above.

During operation, the processor 138 runs a control program 170 held in memory 140 to control the various axes 24, 26, 34, 36, 42, 44, 46, 48, 64, 81, and 84 and to control the x-ray exposure of a patient and to receive and process the image data for display on the flat panel display 116 according to commands received through the control handle 120 and touch screen panel 118.

The memory 140 may also hold a hardware configuration file 160 and one or more personality files 162. The hardware configuration file 160 stores data on the various components as shown in FIG. 6 that have been assembled together to produce the particular positioner 10. The personality files 162 contain models for how the x-ray system will operate, for example, emulating a fluoroscopy system with a spot film device or C-arm type configuration. Each of the personality files 162 includes a zero configuration variable describing how the positioner 10 should be initialized prior to patient scan. More generally, the personality files 162 may include one or more predefined procedures involving dynamic movement of the arms 18 and 20 for a particular procedure such as tomography. The personality files 162 also define how the control handle 120 will be interpreted to axes movement.

For example, it may be desired to operate the positioner to emulate a fluoroscopy machine with a C-arm type structure. In this case, fluoroscopy C-arm type personality files 162 would be loaded and invoked through touch screen panel 118.

Figure 8:
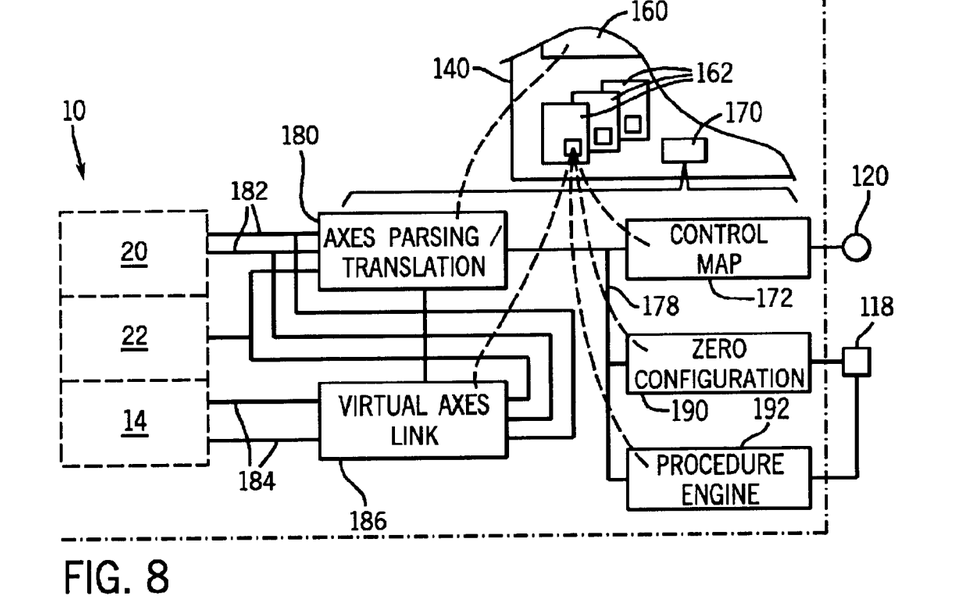
FIG. 8 is a functional diagram of tasks implemented by the controller of FIG. 7 to control the axes according to one embodiment of the invention.

Referring now to FIG. 8, the control program 170 makes use of the configuration file 160 and the personality files 162 to implement control function blocks for the operation of the positioner 10. A first function block provides a control map 172 mapping movements of the control handle 120 to movements in a room coordinate system. For example, if the positioner 10 is programmed to emulate a C-arm type device, rotation of the control handle 120 may cause angulation of the C-arm effectively rotating the central rays 13 and 15 about a center point 174 shown in FIG. 7. The center point may be defined by the center of the base 22 or be arbitrarily located through multiple axis motion as determined by the personality file 162. Vertical and horizontal movement of the control handle 120 may raise or move laterally the virtual C-arm simultaneously moving the x-ray source 12 and x-ray detector 14 as if they were connected by a rigid bar. The assignment of the control handle 120 to particular room coordinates is arbitrary and even in this case, for example, they may be assigned differently with vertical movement of the control handle 120 changing source-to-detector distance rather than raising or lowering the x-ray detector 14 and x-ray source 12 in unison. Likewise, the motion of the positioner components with respect to each other may be arbitrarily defined to simulate positioners of varying geometries.

The control map 172 produces commands 178 in room coordinates or virtual machine coordinates (the latter which describe motion of machine components, such as a C-arm which do not in fact exist). The commands 178 are received by axis parsing and translation module 180 which interrogates the hardware configuration file 160 to see what axes are available in order to realize the coordinate commands 178. Generally there will be more than one combination of different axes movements and the axis parsing and translation module 180 will select among these looking at other considerations, for example, accessibility and the avoidance of collision within the patient space.

The axis parsing and translation module 180 translates the commands 178 into positioner axes commands 182 which are provided to one of the arms, preferably 20. The second arm 18 will receive positioner axis coordinates 184 from a virtual axis link 186. The virtual axis link 186 receiving as inputs the positioner axes commands 182 from the axis parsing and translation module 180 and providing corresponding positioner axis commands 184 to achieve the desired virtual linkage between the x-ray source 12 and x-ray detector 14 as defined by the configuration file 160 and the personality files 162. Generally this linkage will amount to simulation of a virtual structure directly connecting the x-ray source 12 and x-ray detector 14 together such as a bar or C-arm or the like.

Because the arms 18 and 20 are not so connected, a variety of other personalities may be adopted including those which provide for complex independent movement of the x-ray source 12 and x-ray detector 14 for tomography and the like.

As mentioned, a zero configuration variable may be read by the control program 170 to determine the starting position of the positioner 10, e.g., whether the x-ray source 12 and x-ray detector 14 are positioned horizontally with respect to each other or laterally or for a standing patient or the like. Zero configuration task 190 handles this initialization of the axes making use of the hardware configuration file 160 and the particular machine model in personality files 162. The program 170 may also implement a procedure engine 192 which records particular procedures including techniques, exposure times, motion and positioning of the arms that may be collected and exchanged by physicians or skilled practitioners. These procedures may be invoked through the touch screen panel 118.

Referring momentarily to FIG. 7, the hardware configuration file 160 and the various personality files 162 may be loaded via the modem 142 and thus the positioner 10 may be configured remotely and users of the positioner 10 may trade different configurations, personality modules and procedures with each other as they are developed.

Figure 9:
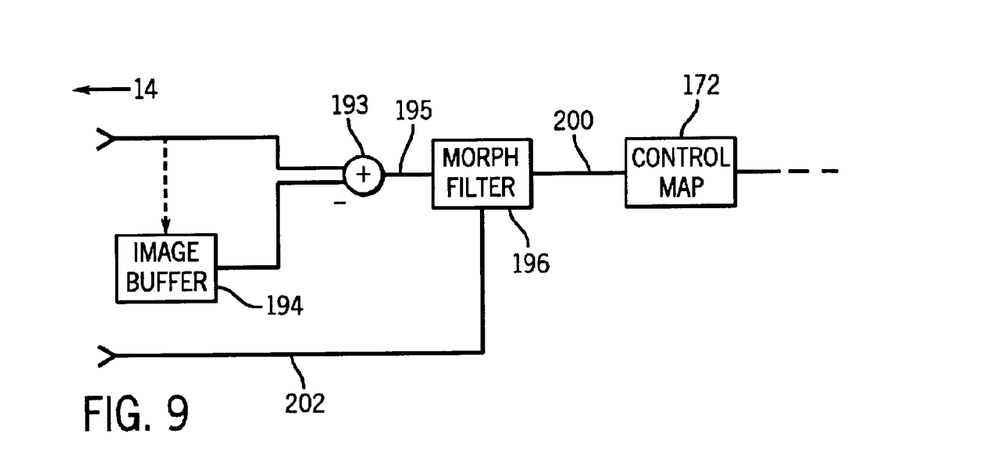
FIG. 9 is a functional diagram task implemented by the controller of FIG. 7 to automatically or semi-automatically track a bolus according to one embodiment of the invention.

Referring now to FIG. 9, one such procedure may receive image data from the x-ray detector 14 into a summing unit 193 implemented by the program 170 and also into an image buffer 194. A subtraction of a previously buffered image and the current image yields motion data 195 which may be operated on by a morphometric filter 196 to identify, for example, a moving bolus of contrast medium in certain types of studies. The morphometric filter may be initialized by user parameters 202 that may be part of a procedure engine module being one of personality files 162.

The location of the bolus relative to the position of the x-ray detector 14 may be extracted as position coordinates 200 in the room or machine frame of reference. The position coordinates 200 may be fed directly to the control map 172 so as to provide for automatic bolus tracking in which the arms 18 and 20 are automatically moved so as to maintain a bolus of contrast medium within the x-ray beam. Memory 140 may also store images including video sequences and the like, user parameter data and other data well known in the art.

Figure 10:
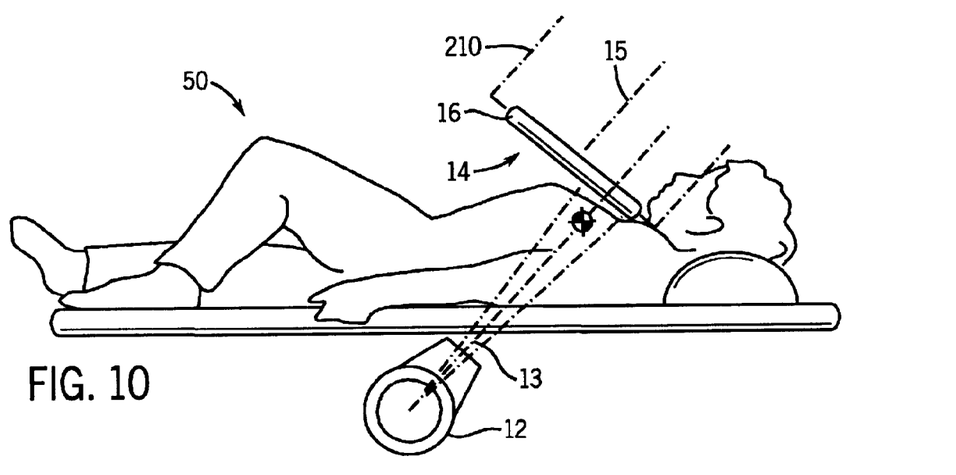
FIG. 10 is a front elevational view of a supine patient showing the x-ray detector and x-ray source positioned by the present invention in the offset opposition.

Referring now to FIG. 10, the small profile of the detector assembly 16 allows for more flexible positioning with respect to patient 50 than would be obtained with a comparable apertured image intensifier 210 shown in dotted outline. This flexibility is further enhanced by the ability to offset the central ray 13 of the x-ray source 12 with respect to the axis 15 of the x-ray detector 14 by displacement of the x-ray source or by offset collimation of the x-ray beam . In either case, when a small beam of x-rays is required, that beam may be directed to a desired area of the x-ray detector 14 rather than to the center of the x-ray detector 14 and that area preferentially scanned. This capability allows improved positioning with respect to the patient 50 without obstruction by the unused areas of the detector assembly 16 for large apertured x-ray detectors 14 or 210 such as may be desirable in particular positioning situations.

Figure 11:
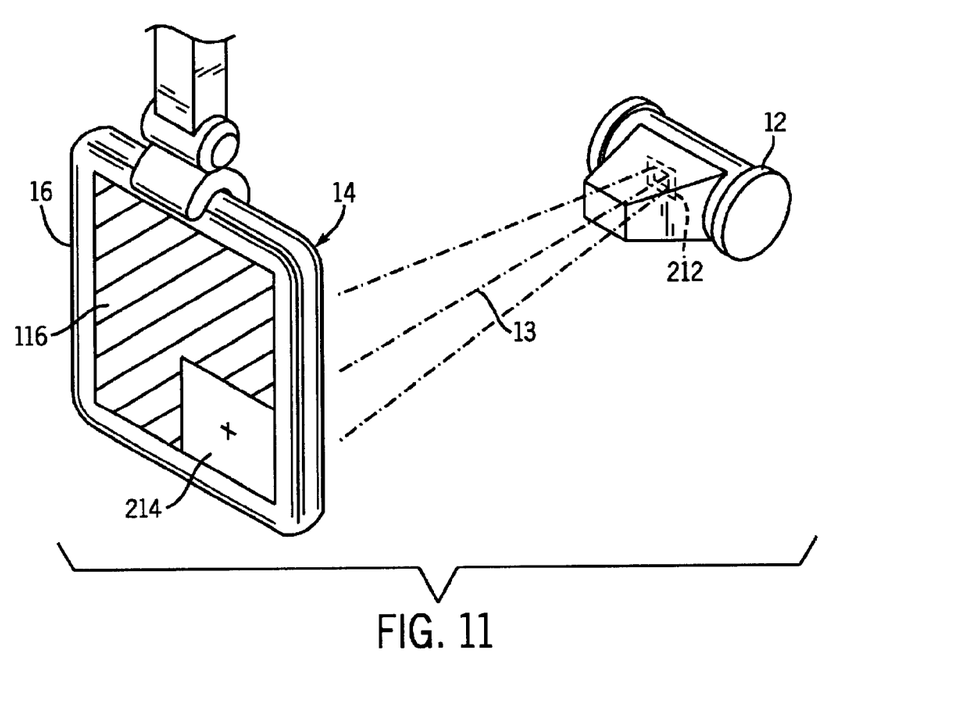
FIG. 11 is a perspective view of the x-ray detector and x-ray source of FIG. 10 showing offset collimation of the x-ray source and a region of interest display shown on the display x-ray detector assembly

Referring to FIG. 11, as mentioned, the displacement of the central ray 13 may be performed by angulation of the x-ray source 12 through additional axes (not shown) or by adjustment of a collimator 212 to collimate the x-ray beam to less than the area of the detector but also to offset the center of the beam toward a detector edge. Control of a collimator 212 to control the exit aperture of the x-ray beam is well known in the art, and is modified only to displace the central ray 13 of the beam. Positioning of the detector assembly 16 may be enhanced by the generation of an x-ray reception pattern 214 on the face of the flat panel display 116, showing the operator the active area of the x-ray detector 14 on the opposite side of the detector assembly 16 prior to exposure.

It is specifically intended that the present invention not be limited to the embodiments and illustrations contained herein, but that modified forms of those embodiments including portions of the embodiments and combinations of elements of different embodiments also be included as come within the scope of the following claims.

What is claimed is:

1. An x-ray imaging system comprising:
   an x-ray source producing an x-ray beam directed along a source axis;
   an x-ray detector assembly including a frame supporting a detector for detecting x-rays received along a detector axis aligned with the source axis, and a user interface mounted to the frame;
   a first and second articulated arm each having at least two independent axes of motion, the first articulated arm holding the x-ray source at its first end, the second articulated arm holding the x-ray detector at its first end;
   at least one extendable x-ray blocking shield connected to the frame that is movable in a longitudinal direction between a retracted and extended configuration via an opening extending through a first end of the frame.

2. The x-ray imaging system as recited in claim 1, further comprising a second stationary x-ray blocking shield mounted to the frame between the detector and the interface.

3. The x-ray imaging system as recited in claim 1, further comprising a pair of guide rails extending longitudinally within the detector assembly, wherein lateral ends of the shield are supported by the guide rails.

4. The x-ray imaging system as recited in claim 1, further comprising a roller mounted to the frame and supporting the shield.

5. The x-ray imaging system as recited in claim 4, wherein the roller is disposed at an opposite end of the frame from the opening.

6. The x-ray imaging system as recited in claim 4, wherein the roller is disposed proximal the opening.

7. The x-ray imaging system as recited in claim 1, wherein the shield is disposed between the detector and the interface when in the retracted configuration.

8. The x-ray imaging system as recited in claim 1, further comprising a bracket that is pivotally mounted to the detector assembly, wherein the shield is supported by the bracket when in the extended configuration.

9. The x-ray imaging system as recited in claim 1, further comprising a bracket that is mounted to the detector assembly and configured for lateral movement with respect thereto, wherein the shield is supported by the bracket when in the extended configuration.

10. The x-ray imaging system as recited in claim 1, wherein the shield assumes a U-shaped configuration when retracted.

11. The x-ray imaging system as recited in claim 10, wherein the shield comprises a first portion extending across the user interface and a second portion that is extendable beyond the detector assembly.

12. The x-ray imaging system as recited in claim 1, further comprising a second x-ray blocking shield extendable through an opening in a second end of the frame opposite the first end.

13. The x-ray imaging system as recited in claim 1, wherein the shield is a lead shield.

14. An integrated x-ray imaging detector assembly for use in an x-ray imaging system, the detector assembly comprising:
  a support frame;
  an x-ray detector module supported by the frame and operable to receive a beam of x-rays emitted from an x-ray source and passed through a target along a detector axis, and further operable to produce electrical signals in response to the received beam of x-rays;
  a display terminal supported by the frame and disposed behind the detector module with respect to the direction of x-ray beam travel, the display terminal being configured to receive the electrical signals and produce an output image corresponding to the electrical signals; and
  at least one extendable x-ray blocking shield connected to the frame that is movable in a longitudinal direction between a retracted and extended configuration via an opening extending through the frame.

15. The x-ray imaging detector assembly as recited in claim 14, wherein the display terminal is aligned with the beam of source x-rays.

16. The x-ray imaging detector assembly as recited in claim 14, wherein the display terminal is rotatable with respect to the support frame while maintaining registration between the image and the detector module.

17. The x-ray imaging detector assembly as recited in claim 14, further comprising a second x-ray blocking shield disposed between the x-ray detector and the display terminal and extending substantially parallel therewith.

18. The x-ray imaging detector assembly as recited in claim 14, wherein the display is a flat panel display.

19. The x-ray imaging detector assembly as recited in claim 14, wherein the support frame is supported by an articulated arm that has at least two independent axes of motion with respect to the target.

20. The x-ray imaging detector assembly as recited in claim 1, wherein the image is viewable while the display terminal extends normally with respect to the detector axis and is aligned with the detector module.

* * * * *

UNITED STATES PATENT AND TRADEMARK OFFICE
CERTIFICATE OF CORRECTION

PATENT NO.   : 6,554,472 B1
DATED        : April 29, 2003
INVENTOR(S)  : Douglas P. Dietz and Michael J. Barber It is certified that error appears in the above-identified patent and that said Letters Patent is hereby corrected as shown below:

Column 5,
Line 24, "18" should read -- 118 --

Column 6,
Lines 42 and 61, "109"" should read -- 109' --
Lines 43, 45, 48 and 67, "108"" should read -- 108' --.

Column 7,
Lines 1 and 40, "108"" should read -- 108' --
Lines 6, 18 and 21, "109""" should read -- 109" --
Lines 11, 14, 15, 19, 22, 23, 26, 30 and 41, "108""" should read -- 108" --
Line 20, "109"" should read -- 109' --

Signed and Sealed this

Sixteenth Day of September, 2003

JAMES E. ROGAN
*Director of the United States Patent and Trademark Office*